United States Patent
Levin et al.

(10) Patent No.: US 12,050,246 B2
(45) Date of Patent: Jul. 30, 2024

(54) DETECTING ASYMMETRY IN A BIDIRECTIONAL SEMICONDUCTOR DEVICE

(71) Applicant: BIOSENSE WEBSTER (ISRAEL) LTD., Yokneam (IL)

(72) Inventors: Michael Levin, Haifa (IL); Yevgeny Bonyak, Haifa (IL); Eyal Rotman, Kiriat Tivon (IL); Alik Vilensky, Netanya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 1109 days.

(21) Appl. No.: 16/876,478

(22) Filed: May 18, 2020

(65) Prior Publication Data

US 2021/0356512 A1 Nov. 18, 2021

(51) Int. Cl.
| | | |
|---|---|---|
| *A61N 1/37* | (2006.01) | |
| *A61N 1/39* | (2006.01) | |
| *G01R 31/28* | (2006.01) | |
| *A61B 18/00* | (2006.01) | |
| *A61B 18/04* | (2006.01) | |

(52) U.S. Cl.
CPC .............. *G01R 31/2837* (2013.01); *A61B 2018/00577* (2013.01); *A61B 18/04* (2013.01); *A61N 1/3706* (2013.01); *A61N 1/3937* (2013.01)

(58) Field of Classification Search
CPC .............. A61N 1/3706; A61N 1/3937
See application file for complete search history.

(56) References Cited

U.S. PATENT DOCUMENTS

| | | | | |
|---|---|---|---|---|
| 3,618,615 | A * | 11/1971 | Greatbatch | A61N 1/3708 |
| | | | | 607/28 |
| 3,619,774 | A * | 11/1971 | Landwehr | H04B 3/46 |
| | | | | 324/613 |
| 3,663,954 | A | 5/1972 | Alker | |
| 5,402,884 | A | 4/1995 | Gilman | |
| 2003/0171793 | A1 | 9/2003 | Carter | |
| 2003/0208248 | A1 | 11/2003 | Carter | |
| 2008/0243074 | A1 | 10/2008 | Miesel | |
| 2011/0196245 | A1* | 8/2011 | Poupko | A61B 5/02028 |
| | | | | 600/506 |
| 2013/0069679 | A1* | 3/2013 | McIntyre | A61N 1/3931 |
| | | | | 324/750.3 |
| 2016/0367305 | A1 | 12/2016 | Hareland | |
| 2017/0020405 | A1 | 1/2017 | Peterson | |
| 2018/0078766 | A1* | 3/2018 | Matolin | A61N 1/36046 |
| 2018/0369597 | A1 | 12/2018 | Anderson | |
| 2020/0138512 | A1 | 5/2020 | Beeckler | |

OTHER PUBLICATIONS

European Search Report for corresponding EPA No. 21174147.5 dated Oct. 14, 2021.

* cited by examiner

*Primary Examiner* — William J Levicky

(57) ABSTRACT

A system includes a signal generator, configured to pass a generated signal, which has two different generated frequencies, through a circuit including a bidirectional semiconductor device. The system further includes a processor, configured to identify, while the generated signal is passed through the circuit, a derived frequency, which derives from the generated frequencies, on the circuit, and to generate, in response to identifying the derived frequency, an output indicating that a property of the bidirectional semiconductor device is asymmetric. Other embodiments are also described.

15 Claims, 3 Drawing Sheets

DETECTING ASYMMETRY IN A BIDIRECTIONAL SEMICONDUCTOR DEVICE

CROSS-REFERENCE TO RELATED APPLICATION

The present application is related to another application entitled "TESTING ELECTRODE QUALITY", filed on even date herewith, whose disclosure is incorporated herein by reference.

FIELD OF THE INVENTION

The present invention is related to the field of electronic circuitry, particularly for medical applications.

BACKGROUND

In many applications, symmetric bidirectional semiconductor devices control the flow of electric current through a circuit.

SUMMARY OF THE INVENTION

There is provided, in accordance with some embodiments of the present invention, a system including a signal generator, configured to pass a generated signal, which has two different generated frequencies, through a circuit including a bidirectional semiconductor device. The system further includes a processor, configured to identify, while the generated signal is passed through the circuit, a derived frequency, which derives from the generated frequencies, on the circuit. The processor is further configured to generate, in response to identifying the derived frequency, an output indicating that a property of the bidirectional semiconductor device is asymmetric.

In some embodiments, the processor is configured to identify the derived frequency over an electrophysiological channel belonging to the circuit.

In some embodiments, the derived frequency is within a bandwidth of an electrophysiological signal carried over the electrophysiological channel.

In some embodiments, each of the generated frequencies is outside the bandwidth.

In some embodiments, the property includes an impedance.

In some embodiments, the derived frequency is a difference between the generated frequencies.

In some embodiments, the processor is further configured to disable a power source connected to the circuit in response to detecting the derived frequency.

In some embodiments, the power source is selected from the group of power sources consisting of: a cardiac defibrillator, a cardiac pacer, and an ablation generator.

In some embodiments, the bidirectional semiconductor device belongs to a voltage suppressor.

In some embodiments, the bidirectional semiconductor device belongs to a semiconductor switch.

There is further provided, in accordance with some embodiments of the present invention, a method including passing a generated signal, which has two different generated frequencies, through a circuit including a bidirectional semiconductor device. The method further includes, while passing the two generated signals through the circuit, identifying a derived frequency, which is derived from the generated frequencies, on the circuit. The method further includes, in response to identifying the derived frequency, generating an output indicating that a property of the bidirectional semiconductor device is asymmetric.

There is further provided, in accordance with some embodiments of the present invention, a system including a signal generator, configured to pass a generated signal, which has two different generated frequencies, through a circuit including an intrabody electrode. The system further includes a processor, configured to identify, while the generated signal is passed through the circuit, a derived frequency, which is derived from the generated frequencies, on the circuit. The processor is further configured to generate, in response to identifying the derived frequency, an output indicating a flaw in the electrode.

In some embodiments, the derived frequency is a difference between the generated frequencies.

In some embodiments, each of the generated frequencies is less than 100 Hz.

In some embodiments, an amplitude of the generated signal is less than 50 µA.

In some embodiments, the signal generator is configured to pass the generated signal through the circuit while the electrode is submerged in an electrolytic solution.

In some embodiments, the electrolytic solution includes saline.

In some embodiments, the electrode belongs to an intrabody probe.

In some embodiments, the system further includes a kit including:
    the signal generator; and
    an electrical interface configured to connect the electrode to the signal generator by connecting the kit to the probe.

In some embodiments, the kit further includes a communication interface, and the processor is configured to identify the derived frequency by processing an output signal received from the kit via the communication interface.

In some embodiments, the electrode is one of a plurality of electrodes belonging to the probe, and the kit further includes a multiplexer configured to selectively connect the electrodes to the signal generator.

There is further provided, in accordance with some embodiments of the present invention, a method including passing a generated signal, which has two different generated frequencies, through a circuit including an intrabody electrode. The method further includes, while passing the generated signal through the circuit, identifying a derived frequency, which is derived from the generated frequencies, on the circuit. The method further includes, in response to detecting the derived frequency, generating an output indicating a flaw in the electrode.

BRIEF DESCRIPTION OF THE DRAWINGS

The present invention will be more fully understood from the following detailed description of embodiments thereof, taken together with the drawings, in which.

DETAILED DESCRIPTION OF EMBODIMENTS

Glossary

Figure 1:
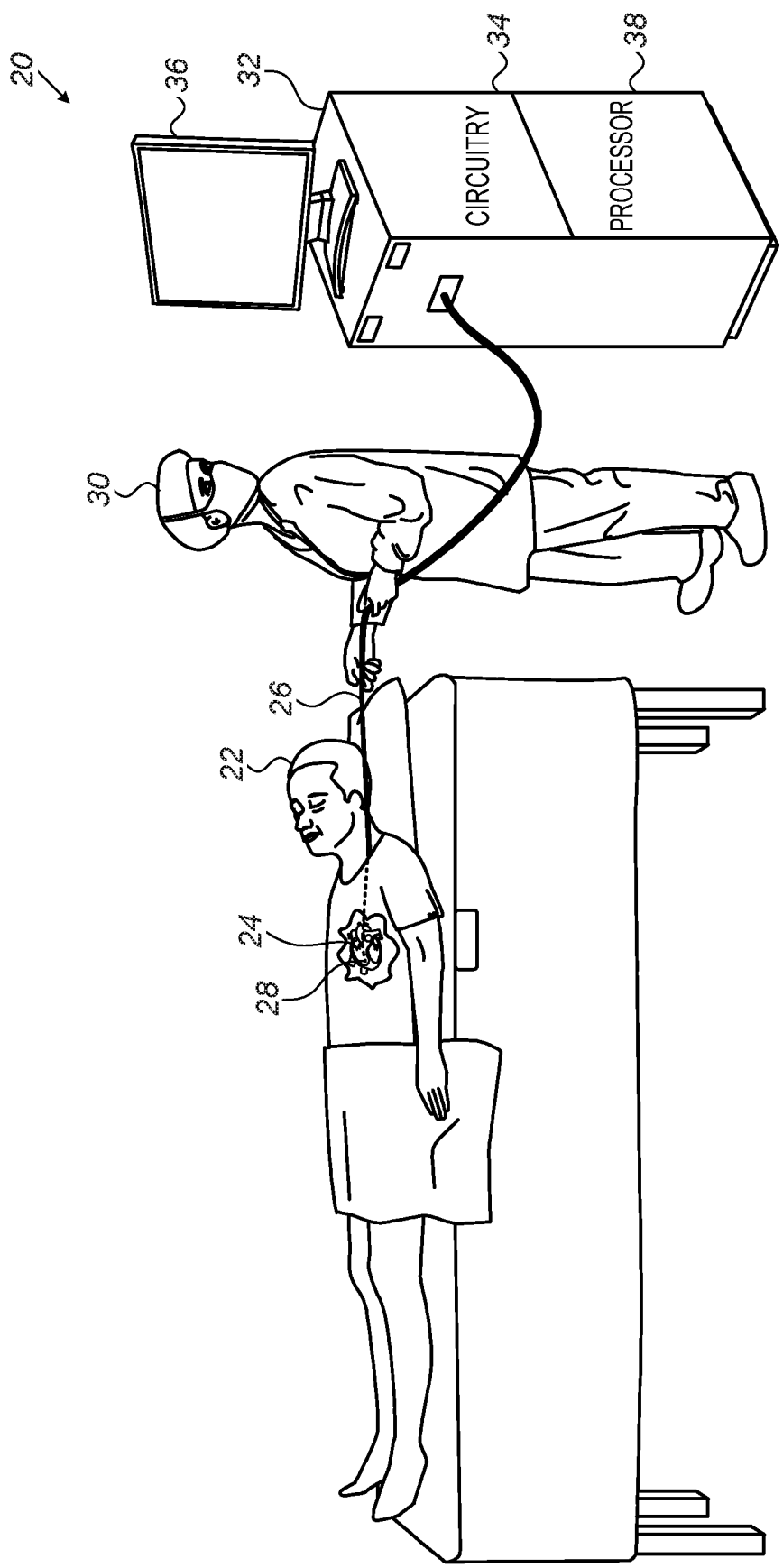
FIG. 1 is a schematic illustration of an electrophysiological system, in accordance with some exemplary embodiments of the present invention.

In the context of the present application, including the claims, the term "bidirectional semiconductor device" may refer to any semiconductor device configured to conduct both the positive and negative portions of an alternating current (AC) signal. If a property (e.g., the impedance) of the bidirectional semiconductor device is the same for both portions of the signal, the property (or the device itself) is said to be "symmetric;" otherwise, the property (or the device itself) is said to be "asymmetric."

Overview

In many cases, it is desired that a bidirectional semiconductor device in a circuit have symmetric properties, such that an alternating current (AC) passing through the device does not generate any direct current (DC) voltage. For a circuit connected to an intrabody probe, such as an electrophysiological probe, disposed within the body of a subject, this symmetry is particularly important, as any DC voltages generated, for example, from the flow of ablative radiofrequency (RF) currents through the bidirectional semiconductor device, are likely to be dangerous to the subject. Hence, there is a need for fast and effective detection of any asymmetry in a bidirectional semiconductor device.

To address this need, exemplary embodiments of the present invention provide a system for testing the symmetry of a bidirectional semiconductor device in a circuit. The system comprises a signal generator connected to the circuit and configured to generate a signal having two different frequencies. Provided that the bidirectional semiconductor device is symmetric, the bidirectional semiconductor device behaves as a linear device, and hence does not generate any additional frequencies. However, in the event that the bidirectional semiconductor device is asymmetric (e.g., by virtue of having an asymmetric impedance), the device behaves non-linearly, thus causing other "derived" frequencies, which derive from the frequencies of the generated signal, to be carried on the circuit. Hence, by identifying one of these derived frequencies, such as the difference between the frequencies of the generated signal, the asymmetry may be detected.

Advantageously, for electrophysiological applications, the derived frequencies may be detected over a preexisting electrophysiological channel, such that the symmetry testing described herein may not require additional hardware. To facilitate this, the frequencies of the generated signal may be chosen such that the difference between the frequencies falls within the bandwidth of the electrophysiological signal carried over the channel. Nonetheless, the frequencies themselves may be chosen to fall outside this bandwidth, such that the generated signal does not interfere with the detection of the electrophysiological signal.

Exemplary embodiments of the present invention further provide a testing kit for testing the quality of an electrode while the electrode is submerged in an electrolytic solution. The kit, which comprises the aforementioned signal generator, is connected to the electrode, such that the generated signal flows through the electrode. In the event of a flaw in the surface of the electrode (e.g., in the event that the surface is rough or dirty), the non-linearity of the interface between the electrode and the electrolytic solution is increased, such that the amplitude with which derived frequencies are generated is also increased. Hence, by identifying one of the derived frequencies, the flaw may be detected.

Although the present description mainly relates to electrophysiological applications, it is emphasized that embodiments of the present invention may be used to test the symmetry of any bidirectional semiconductor device, and to test the quality of any electrode.

System Description

Reference is initially made to FIG. 1, which is a schematic illustration of an electrophysiological system 20, in accordance with some exemplary embodiments of the present invention.

System 20 comprises an intrabody probe 26, comprising one or more intrabody electrodes 28 disposed at the distal end thereof. Using probe 26 and electrodes 28, a physician 30 may acquire electrophysiological signals from a subject 22, such as electrogram signals from the heart 24 of subject 22. Alternatively or additionally, the physician 30 may use the probe 26 and electrodes 28 to pace or to defibrillate heart 24, or to ablate tissue of the heart 24.

Probe 26 is proximally connected to circuitry 34, which is typically contained in a console 32. Typically, system 20 further comprises a processor 38 and a monitor 36. In response to output from circuitry 34, processor 38 may display relevant output on monitor 36, as further described below with reference to FIG. 2.

In general, processor 38 may be embodied as a single processor, or as a cooperatively networked or clustered set of processors. In some exemplary embodiments, the functionality of processor 38, as described herein, is implemented solely in hardware, e.g., using one or more Application-Specific Integrated Circuits (ASICs) or Field-Programmable Gate Arrays (FPGAs). In other exemplary embodiments, the functionality of processor 38 is implemented at least partly in software. For example, in some exemplary embodiments, processor 38 is embodied as a programmed digital computing device comprising at least a central processing unit (CPU) and random-access memory (RAM). Program code, including software programs, and/or data are loaded into the RAM for execution and processing by the CPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Figure 2:
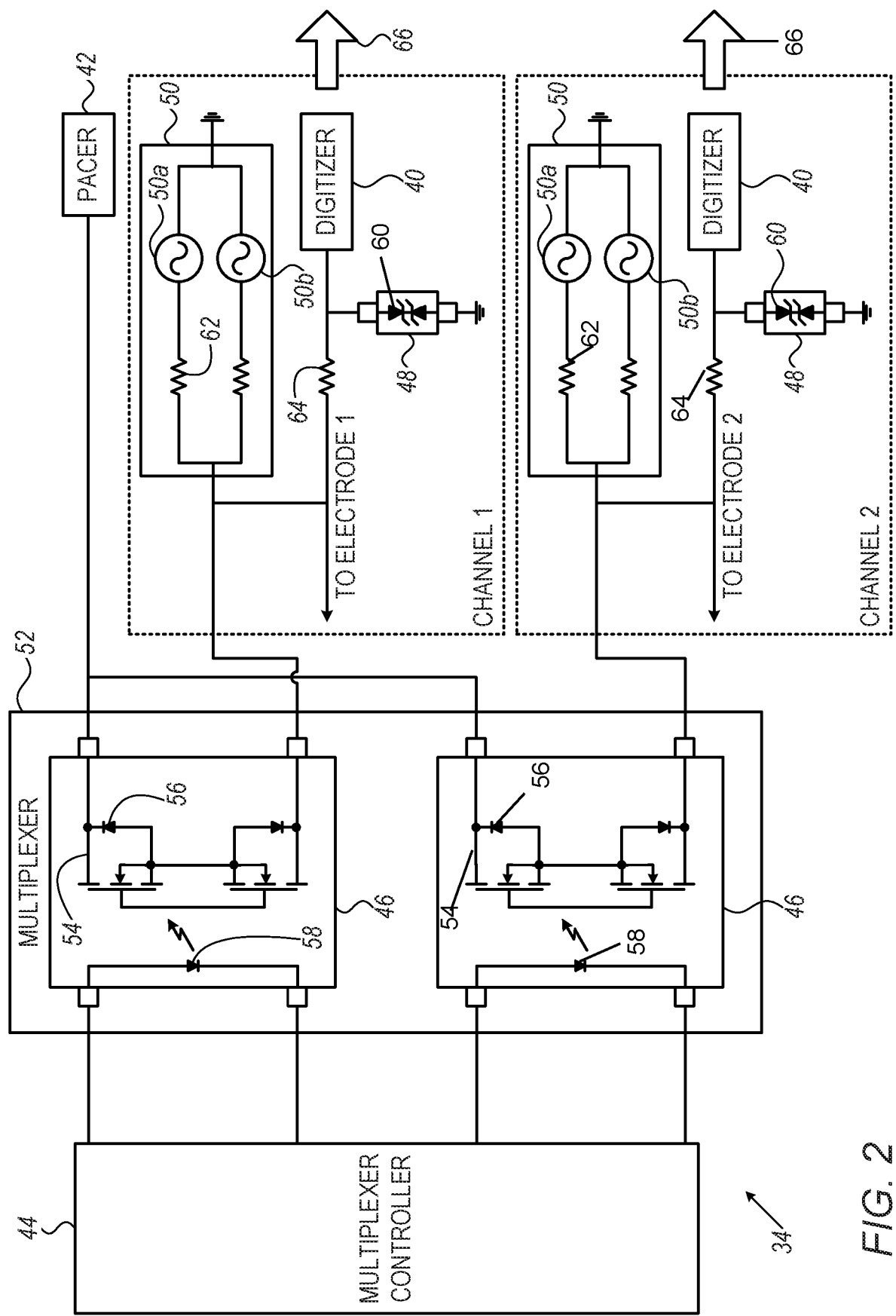
FIG. 2 is a schematic illustration of circuitry, in accordance with some exemplary embodiments of the present invention.

Reference is now made to FIG. 2, which is a schematic illustration of circuitry 34, illustrated in FIG. 1, in accordance with some exemplary embodiments of the present invention.

Circuitry 34 comprises at least one digitizer 40, configured to digitize electrophysiological signals from the electrodes 28 and to output the digitized signals 66 to processor 38 (FIG. 1) over a wired or wireless connection. Digitizer 40 may comprise any suitable filters for filtering the signals prior to digitization.

Typically, circuitry 34 further comprises at least one power source configured to deliver power to the electrodes. For example, circuitry 34 may comprise a cardiac pacer 42, a cardiac defibrillator, and/or an ablation generator. Typically, the circuitry further comprises at least one voltage suppressor 48, which suppresses voltages delivered by the power source.

For exemplary embodiments in which the probe comprises multiple electrodes, the circuitry typically comprises different respective electrophysiological channels for the electrodes. Each channel comprises a separate digitizer 40 and voltage suppressor 48, which are typically connected to the electrode, in parallel to one another, via a resistor 64. Circuitry 34 may further comprise a multiplexer 52, which comprises multiple semiconductor switches 46, and a multiplexer controller 44. Multiplexer controller 44 is configured to control switches 46 so as to selectively connect the channels to the power source.

In general, the circuitry may comprise any number of electrodes, and hence, any number of channels. By way of example, FIG. 2 shows an embodiment in which the probe comprises two electrodes, referred to in the figure as "electrode 1" and "electrode 2," and circuitry 34 correspondingly comprises two channels, referred to in the figure as "channel 1" and "channel 2."

Circuitry 34 comprises at least one bidirectional semiconductor device.

For example, each switch 46 may comprise a bidirectional semiconductor device. As a specific example, each switch 46 may comprise a light-emitting diode (LED) 58 along with a pair of phototransistors 54 connected to one another and to a pair of parasitic diodes 56. In response to a control signal from multiplexer controller 44, LED 58 may emit light toward phototransistors 54, thus causing the phototransistors to become conductive. Current (e.g., from pacer 42) may then flow through the switch.

Alternatively or additionally, each voltage suppressor 48 may comprise a bidirectional semiconductor device. For example, each voltage suppressor 48 may comprise a pair of diodes 60 or thyristors connected to one another, in series or in parallel, in opposing orientations. Diodes 60 may comprise avalanche or Zener diodes, for example.

Advantageously, circuitry 34 is configured to test the symmetry of any of the bidirectional semiconductor devices belonging to the circuitry. To facilitate this testing, the circuitry comprises at least one signal generator 50 configured to generate a signal having a first frequency f1 and a second frequency f2. Typically, the amplitude of the generated signal is relatively low, such as less than 10 μA, so as not to pose a risk to the subject. In the event that the impedance or another property (e.g., the cutoff voltage) of one of the bidirectional semiconductor devices is asymmetric, the device behaves non-linearly, thus generating other frequencies derived from f1 and f2, such as frequencies that are linear combinations of f1 and f2. By identifying one of these other frequencies, such as the beat frequency |f1−f2|, f1+f2, 2f1+f2, or |2f1−f2|, in digitized signal 66, the processor may detect the asymmetry.

In some exemplary embodiments, signal generator 50 comprises a voltage source. In such exemplary embodiments, as shown in FIG. 2, the signal generator may be modeled as a first voltage source 50a, configured to generate a first signal having first frequency f1, and a second voltage source 50b, configured to generate a second signal having second frequency f2, each of the voltage sources being connected in series with a respective resistor 62. In other exemplary embodiments, signal generator 50 comprises a current source.

In some exemplary embodiments, circuitry 34 comprises a different respective signal generator for each channel. In other exemplary embodiments, a single signal generator is connected, via a multiplexer, to all of the channels.

Typically, f1 and f2 lie outside the bandwidth of (i.e., outside the range of frequencies exhibited by) the electrophysiological signal carried over the channel, such that the generated signal does not interfere with the processing of the electrophysiological signal. For example, for applications in which electrogram signals are carried over the channels, each of the generated frequencies may be greater than 500 Hz, such as greater than 1000 Hz. Nevertheless, at least one derived frequency, such as the difference between f1 and f2, is typically within the aforementioned bandwidth, such that the sampling rate of the digitizer, which generally corresponds to the highest frequency in the bandwidth, is sufficient for capturing the derived frequency. For example, for electrogram applications, the derived frequency may be less than 500 Hz, such as between 400 and 500 Hz. Thus, advantageously, the derived frequency may be identified in signal 66, i.e., the regular digitized electrophysiological signal received from digitizer 40.

In response to identifying the derived frequency (e.g., in response to identifying a component of signal 66 having the derived frequency and an amplitude greater than a predefined threshold), the processor may generate an output indicating that the impedance of the bidirectional semiconductor device is asymmetric, e.g., by displaying a suitable warning on monitor 36 (FIG. 1). Alternatively or additionally, in response to identifying the derived frequency, the processor may disable the power source.

Testing Electrode Quality

Figure 3:
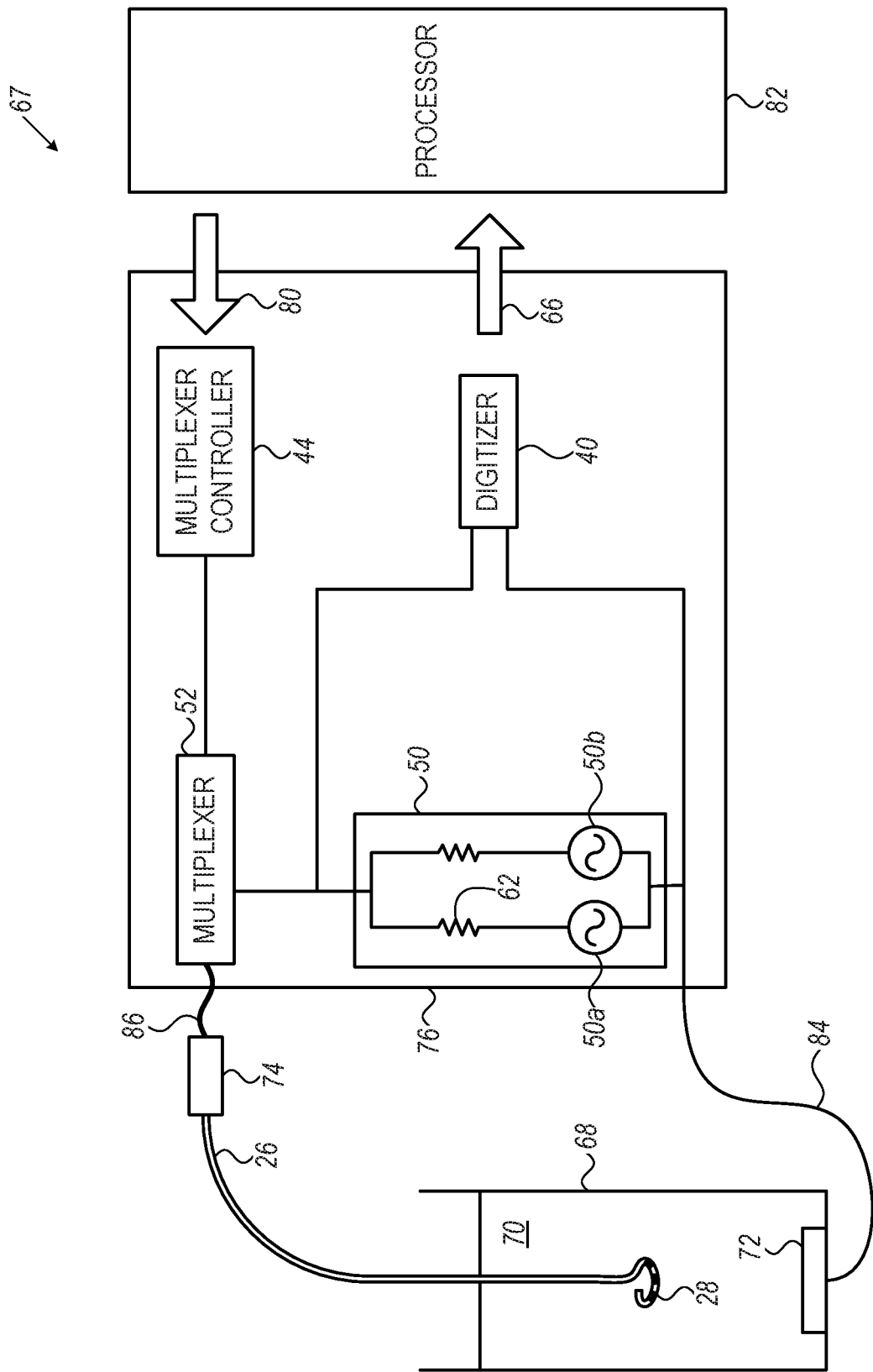
FIG. 3 is a schematic illustration of a system for testing electrode quality, in accordance with some Exemplary embodiments of the present invention.

Reference is now made to FIG. 3, which is a schematic illustration of a system 67 for testing the quality of electrodes 28 prior to the use of probe 26, in accordance with some exemplary embodiments of the present invention.

System 67 comprises signal generator 50, which as set forth above with respect to FIG. 2, may be modeled as a first voltage source 50a, configured to generate a first signal having first frequency f1, and a second voltage source 50b, configured to generate a second signal having second frequency f2, each of the voltage sources being connected in series with a respective resistor 62, and digitizer 40, which is configured to communicate with a processor 82 over a wired or wireless connection. To test each electrode, the generated signal from the signal generator is passed through a circuit including the electrode. While the generated signal is passed through the circuit, processor 82 monitors the circuit for a derived frequency, such as |f1−f2|, by processing digitized signal 66, as described above with reference to FIG. 2. In response to identifying the derived frequency (e.g., in response to identifying a component of signal 66 having the derived frequency and an amplitude greater than a predefined threshold), the processor 82 generates an output indicating a flaw in the electrode.

Typically, the signal generator and digitizer belong to a testing kit 76 configured to connect to the probe 26, e.g., to the proximal end thereof. Typically, testing kit 76 further comprises multiplexer 52 (which may comprise switches of any type) and multiplexer controller 44. Each switch in multiplexer 52 is configured to connect, via a different respective wire, to a different respective electrode at the distal end of the probe 26. The wires may be contained in a cable 86, which may be connected to the probe 26 via a suitable interface in a handle 74 of the probe 26. In response to a control signal 80 from processor 82, multiplexer controller 44 controls multiplexer 52 such that the multiplexer selectively connects the electrodes to the signal generator for testing.

In general, processor 82 may be embodied as a single processor, or as a cooperatively networked or clustered set of processors. In some exemplary embodiments, the functionality of processor 82, as described herein, is implemented solely in hardware, e.g., using one or more Application-Specific Integrated Circuits (ASICs) or Field-Programmable Gate Arrays (FPGAs). In other exemplary embodiments, the functionality of processor 82 is implemented at least partly in software, as described above for processor 38 (FIG. 1). Processor 82 may belong to testing kit 76 or, as implied by FIG. 3, to an external computer. In response to identifying the derived frequency, the processor 82 may display a suitable warning on a computer monitor, output an audio alert, and/or generate another output, such as by activating a warning light belonging to the testing kit.

Typically, electrodes 28 are tested while submerged in an electrolytic solution 70, such as saline, which simulates an intrabody environment. The non-linearity of the impedance at the interface between each electrode and solution 70, and hence, the amplitude of any derived-frequency components of signal 66, increases with the degree to which the surface of the electrode is flawed, e.g., rough or dirty. Hence, as described above, flaws may be detected in response to identifying the derived frequencies in signal 66.

Typically, a return electrode 72, which is typically disposed at the bottom of the container 68 containing solution 70, is connected, via a wire 84, to the testing kit. Wire 84 may be contained in a cable. Thus, the testing circuit through which the generated signal is passed includes solution 70, return electrode 72, and wire 84.

In general, the testing kit may comprise a case made of any suitable material, such as a plastic, configured to hold the various components of the kit described herein. The testing kit may comprise any suitable electrical interface, such as a port or socket, for connecting the kit to the probe such that electrodes 28 are connected to the signal generator. Similarly, the testing kit may comprise any suitable electrical interface for connecting the kit to return electrode 72. Alternatively or additionally, the testing kit may comprise any suitable wired or wireless communication interface (e.g., a Universal Serial Bus (USB) port) for communicating with processor 82, such that the processor may receive signal 66 from the kit, and/or the kit may receive control signal 80 from the processor, via the communication interface.

Typically, frequencies f1 and f2 are relatively small, such as less than 100 Hz, so as to amplify any non-linear response of the electrodes. Also typically, the amplitude of each of the generated signals is relatively small, such as less than 50 μA, so as to minimize any undesired effects on the electrode surfaces.

It will be appreciated by persons skilled in the art that the present invention is not limited to what has been particularly shown and described hereinabove. Rather, the scope of embodiments of the present invention includes both combinations and sub combinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for testing the symmetry of a bidirectional semiconductor device in a circuit, the system comprising:
a signal generator, configured to pass a generated signal, which has two different generated frequencies, through the circuit, wherein the circuit includes:
the bidirectional semiconductor device;
at least one electrode configured for acquiring ECG signals; and
a digitizer configured to digitize the acquired ECG signal, wherein each of the two different generated frequencies are selected to be above an operating bandwidth of the digitizer and wherein a difference between the two generated frequencies is selected to be within the operating bandwidth of the digitizer; and
a processor, configured to:
while the generated signal is passed through the circuit, identify a derived frequency, which derives from the generated frequencies, on the circuit, and
in response to identifying the derived frequency, generate an output indicating that the bidirectional semiconductor device is asymmetric.

2. The system according to claim 1, wherein the output is a measure of an impedance.

3. The system according to claim 1, wherein the derived frequency is a difference between the generated frequencies.

4. The system according to claim 1, wherein the processor is further configured to disable a power source connected to the circuit in response to detecting the derived frequency.

5. The system according to claim 4, wherein the power source is selected from the group of power sources consisting of: a cardiac defibrillator, a cardiac pacer, and an ablation generator.

6. The system according to claim 4, including a plurality of electrodes, wherein the circuit further comprises a multiplexer configured to selectively connect each of the plurality of electrodes to the power source and to disable the power source in response to detecting the derived frequency at any one of a plurality of electrodes.

7. The system according to claim 1, wherein the bidirectional semiconductor device belongs to a voltage suppressor.

8. The system according to claim 1, wherein the bidirectional semiconductor device belongs to a semiconductor switch.

9. A method for testing the symmetry of a bidirectional semiconductor device in a circuit, the method comprising:
passing a generated signal, which has two different generated frequencies, through the circuit wherein the circuit includes:
the bidirectional semiconductor device;
at least one electrode configured for acquiring ECG signals; and
a digitizer configured to digitize the acquired ECG signal,
wherein each of the two different generated frequencies are selected to be above an operating bandwidth of the digitizer and wherein a difference between the two generated frequencies is selected to be within the operating bandwidth of the digitizer;
while passing the two generated signals through the identifying a derived circuit, frequency, which is derived from the generated frequencies, on the circuit; and
in response to identifying the derived frequency, generating an output indicating that the bidirectional semiconductor device is asymmetric.

10. The method according to claim 9, wherein the output is a measure of an impedance.

11. The method according to claim 9, wherein the derived frequency is a difference between the generated frequencies.

12. The method according to claim 9, further comprising, in response to detecting the derived frequency, disabling a power source connected to the circuit.

13. The method according to claim 12, wherein the power source is selected from the group of power sources consisting of: a cardiac defibrillator, a cardiac pacer, and an ablation generator.

14. The method according to claim 9, wherein the bidirectional semiconductor device belongs to a voltage suppressor.

15. The method according to claim 9, wherein the bidirectional semiconductor device belongs to a semiconductor switch.

\* \* \* \* \*